US008138005B2

(12) United States Patent
Jang et al.

(10) Patent No.: US 8,138,005 B2
(45) Date of Patent: Mar. 20, 2012

(54) METHOD FOR FABRICATING NOVEL HIGH-PERFORMANCE FIELD-EFFECT TRANSISTOR BIOSENSOR BASED ON CONDUCTIVE POLYMER NANOMATERIALS FUNCTIONALIZED WITH ANTI-VEGF ADAPTER

(75) Inventors: Jyong Sik Jang, Seoul (KR); Oh Seok Kwon, Seoul (KR); Seon Joo Park, Seoul (KR)

(73) Assignee: Snu R&DB Foundation, Seoul (KR)

( * ) Notice: Subject to any disclaimer, the term of this patent is extended or adjusted under 35 U.S.C. 154(b) by 218 days.

(21) Appl. No.: 12/766,280

(22) Filed: Apr. 23, 2010

(65) Prior Publication Data
US 2011/0237012 A1 Sep. 29, 2011

(30) Foreign Application Priority Data

Mar. 23, 2010 (KR) .................. 10-2010-0025595

(51) Int. Cl.
*H01L 21/00* (2006.01)
(52) U.S. Cl. .............. 438/49; 438/1; 977/742; 977/716; 977/729; 313/311
(58) Field of Classification Search ............... 438/1, 49; 977/714, 716, 729, 737, 936–938; 313/311
See application file for complete search history.

(56) References Cited

U.S. PATENT DOCUMENTS

| 7,692,218 B2 * | 4/2010 | Barron et al. ............... 257/253 |
| 8,058,673 B2 * | 11/2011 | Kim et al. ................. 257/253 |
| 2010/0032653 A1 * | 2/2010 | Takeda et al. .............. 257/24 |

FOREIGN PATENT DOCUMENTS

KR 10-2009-0053494 A 5/2009

OTHER PUBLICATIONS

Resubmission of Jang et al., "Recent Progress in the Development of State-of-Art Sensors Based on Conducting Polymer Nanomaterials", Polymer Science and Technology, vol. 18, No. 4, Aug. 2007, pp. 306-310, with English-language abstract.
Folkman et al., "Angiogenesis", The Journal of Biological Chemistry, vol. 267, No. 16, Jun. 5, 1992, pp. 10931-10934.
Horak et al., "Angiogenesis, assessed by platelet/endothelial cell adhesion molecule antibodies, as indicator of node metastases and survival in breast cancer", The Lancet, vol. 340, Nov. 7, 1992, pp. 1120-1124.

(Continued)

*Primary Examiner* — David Vu
*Assistant Examiner* — Caleb Henry
(74) *Attorney, Agent, or Firm* — Birch, Stewart, Lolasch & Birch, LLP

(57) ABSTRACT

Disclosed is a method for fabricating a high-performance field-effect transistor biosensor for diagnosing cancers using micro conductive polymer nanomaterials funtionalized with anti-VEGF aptamer. Disclosed is a high-sensitivity field-effect transistor biosensor for diagnosing cancers using a micro conductive polymer nanomaterial transistor array including a micro polymer nanomaterial transistor array including a channel region provided with a metal source electrode, a metal drain electrode, a gate and micro polymer nanomaterials, and an anti-VEGF aptamer covalently bound to the surface of the micro polymer nanomaterials constituting the channel region of the micro polymer nanomaterials transistor array, to target VEGF (Vascular endothelial growth factor).

7 Claims, 2 Drawing Sheets

OTHER PUBLICATIONS

Jang et al., "Recent Progress in the Development of State-of-Art Sensors Based on Conducting Polymer Nanomaterials", Polymer Science and Technology, vol. 18, No. 4, Aug. 2007, pp. 306-310.

Klagsbrun et al., "Regulators of Angiogenesis", Annual Reviews Inc., 53, 1991, pp. 217-239.

Lee et al., "Electrical detection of VEGFs for cancer diagnoses using anti-vascular endothelial growth factor aptamer-modified Si nanowire FETs", Biosensors and Bioelectronics, 24, 2009, pp. 1801-1805.

Liu et al., "Polymeric Nanowire Chemical Sensor", American Chemical Society, vol. 4, No. 4, 2004, pp. 671-675.

Macchiarini et al., "Relation of neovascularisation to metastasis of non-small-cell lung cancer", The Lancet, vol. 340, Jul. 18, 1992, pp. 145-146.

McQuade et al., "Conjugated Polymer-Based Chemical Sensors", American Chemical Society, vol. 100, 2000, pp. 2537-2574.

Menon et al., "Investigation of Molecular and Supermolecular Structure in Template-Synthesized Polypyrrole Tubules and Fibrils", American Chemical Society, vol. 8, 1996, pp. 2382-2390.

Swager, "The Molecular Wire Approach to Sensory Signal Amplification", American Chemical Society, vol. 31 No. 5, 1998, pp. 201-207.

Virji et al., Polyaniline Nanofiber Gas Sensors: Examination of Response Mechanisms, American Chemical Society, vol. 4, No. 3, 2004, pp. 491-496.

* cited by examiner

METHOD FOR FABRICATING NOVEL HIGH-PERFORMANCE FIELD-EFFECT TRANSISTOR BIOSENSOR BASED ON CONDUCTIVE POLYMER NANOMATERIALS FUNCTIONALIZED WITH ANTI-VEGF ADAPTER

FIELD OF THE INVENTION

The present invention relates to a method for preparing micro polymer nanomaterials, to which anti-VEGF aptamer selectively bound to vascular endothelial growth factors (VEGFs) is adhered, and a method for fabricating a high-performance field-effect transistor biosensor for diagnosing cancers using the conductive polymer nanomaterials. More specifically, the present invention relates to a method for detecting trace amounts of VEGF present in blood by fixing micropolymer nanomaterials, to which an anti-VEGF aptamer having high affinity to VEGF is chemically bound, on an electrode substrate and real-time monitoring current variation caused by the bond with VEGF in a field-effect transistor array.

BACKGROUND OF THE INVENTION

To date, biosensors have generally used optical measurement methods utilizing optical dyes. Biosensors using optical measurement methods have advantages of considerably excellent sensitivity and superior sensing selectivity, but disadvantages of high-cost measurement apparatuses and long measurement time due to the necessity of pre-treating processes such as adhesion of optical dyes to reagents. In an attempt to solve these disadvantages, a great deal of research is being actively conducted on nano-biosensors. Nano-biosensors are manufactured based on nanotechnology. Nanomaterials such as nanowires or nanoparticles have a considerably large surface area per unit volume, linkable to biomolecules, thus exhibiting considerably superior sensitivity, as compared to conventional micromaterials. Furthermore, biosensors using materials such as optical dyes indirectly measure biomaterials through light for a long time, whereas nanobiosensors can advantageously rapidly real-time monitor sensitivity through direct binding of nanomaterials to target biomaterials.

Research associated with nanomaterials for biosensors is actively conducted based on carbon nanotubes, and metal and inorganic semiconductor nanomaterials. Carbon nanotubes are continuously researched by development of various synthesis methods, but have not been put into practical application due to disadvantages such as high manufacturing costs, chirality-dependent electrical properties and inactive surfaces. In addition, metal and inorganic semiconductor nanomaterials are limited in terms of biocompatibility due to toxicity. On the other hand, conductive polymers have various advantages such as various molecule designs, easy processing, low-weight and flexibility (Polymer Science and Technology, vol. 18, pp. 306-310, 2007).

The oxidation level of conductive polymers can be readily controlled by chemical or electrochemical doping/dedoping. This induces sensitive rapid reactions (variations in electrical conductivity or color) with specific chemical and biological species (See: Chem. Rev., vol. 100, pp. 2537-2574, 2000). This property enables application of conductive polymers to various sensor activities. In practical use, conductive polymers are known to be more sensitive to external environmental variations than other sensing materials due to inherent transfer properties such as such as electrical conductivity and energy transfer (See: Acc. Chem. Res., vol. 31, pp. 201-207, 1998). In addition, one-dimensional conductive polymer nanostructures such as nanorods, nanofibers and nanotubes have a larger surface area, thus providing sensitivity and real-time reactions amplified by increased interaction with analytes (See: Nano Lett., vol. 4, pp. 491-496,2004; Nano Lett., vol 4, pp. 671-675, 2004). In spite of these advantages, the absence of reproducible and reliable methods for preparing nanoparticles has hampered development of sensors using conductive polymer nanostructures. In particular, methods for fabricating conductive polymer nanomaterials have been limited to methods using expensive templates such as porous alumina membranes or polycarbonate membranes, and have a serious disadvantage of considerably low yield through complicated multi-step synthesis (See: Chem. Mater., vol. 8, pp. 2382-2390; Science, vol. 296, pp. 1997).

In general biosensors, for reactions selective to specific target materials, receptors, RNA/DNA aptamers, proteins, or the like are incorporated into transducers. Receptors are generally adhered to the surface of transducers through absorption, entrapment and covalent bonding. Of these, the method for adhering receptors through covalent bonding has an advantage of considerably superior chemical and physical stability as compared to other methods. However, this method requires chemical functional groups applicable to the surface of transducers. Metal, inorganic semiconductor and polymer nanomaterials as well as carbon nanotubes have inactive surfaces, thus requiring additional surface-treatment processes to incorporate surface functional groups.

Probing and detection of biomaterials are currently carried out in solution. For this purpose, carbon nanotubes and inorganic semiconductor nanomaterials are directly fixed on an electrode surface by photolithography or electron-beam lithography. However, conductive polymer nanomaterials are disadvantageously unsuitable for lithography due to the risk of chemical and physical damage. In addition, most conductive polymers exhibit low adhesion force to an electrode substrate made of a material such as silicon, glass, or metal. Due to these disadvantages, development of biosensors using conductive polymer nanostructures has been considerably limited.

The recently discovered vascular endothelial growth factor (hereinafter, referred to as "VEGF") is an endothelial cell-specific mitosis accelerant known as an important inducing factor which mediates generation mechanisms and formation of blood vessels under physiological or pathological conditions and creates new blood vessels in a variety of tumors. It has already been demonstrated that such blood vessel formation is related to pathogenesis of various diseases. Such diseases include ocular neovascular syndrome, rheumatoid arthritis and psoriasis such as solid tumors, proliferative retinopathy or age-related macular degeneration (AMD) (Documents ([Folkman et al. J. Biol. Chem. 267:10931-10934 (1992)]; [Klagsbrun et al. Annu Rev. Physiol. 53:217-239 (1991)]; and [Garner A, Vascular diseases. In: Pathobiology of ocular disease: a dynamic approach. Garner A, Klintworth G K, Eds. 2nd Edition (Marcel Dekker, NY, 1994), pp 1625-1710])). For solid tumors, creation of new blood vessels causes tumor cells to exhibit superior development superiority and proliferation autonomy, as compared to normal cells. Accordingly, for breast cancers and other tumors, correlation between microvessel density of the tumor sites and patient survival rate was reported (Documents ([Weidner et al. N Engl J Med 324:1-6 (1991)]; [Horak et al. Lancet 340:1120-1124 (1992)]; and [Macchiarini et al. Lancet 340:145-146 (1992)])). As such, VEGF plays an essential role in development of various tumor cells and is detected in large amounts where tumors are created. Accordingly, accurate sites and rapid diagnosis of formed tumors can be realized by detecting VEGF amount variations. Biosensors for detecting various VEGFs have been developed to date (Biosens Bioelectron 2009; 24:1801-05). However, to date, there is a need for continuous development of biosensors due to disadvantages such as limited detection concentration and long detection time.

Accordingly, for industrial application of basic technologies, there is an increasing need for technologies for efficiently and simply controlling diameters of conductive polymer nanomaterials having surface chemical functional groups and technologies for fabricating high-performance biosensors based on the same.

SUMMARY OF THE INVENTION

Therefore, the present invention has been made to solve the above and other technical problems that have yet to be resolved.

It is one object of the present invention to provide a method for preparing micro conductive polymer nanomaterials having a functionalized surface controlled by copolymerizing conductive polymer monomers and functional monomers in the presence of a reverse phase emulsion.

It is another object of the present invention to provide a method for fabricating a high-sensitivity field-effect transistor biosensor for diagnosing cancers, selectively bound to VEGF (target), by fixing micro conductive polymer nanomaterials prepared using the surface functional groups on an electrode substrate and adhering an anti-VEGF aptamer to the surface of nanomaterials through covalent bonding.

As a result of a variety of extensive and intensive studies and experiments to solve the problems as described above, the inventors of the present invention have developed a method, which is entirely different from known methods, that is, a method for fixing micro polymer nanomaterials through chemical bonding on an electrode substrate which is surface-modified with functional groups incorporated by copolymerization (Korean Patent Application No. 10-2007-0120359) and then developed biosensors for detecting VEGF with improved performance, as compared to conventional biosensors for diagnosing VEGF, based on the same. In addition, the present inventors confirmed that field-effect transistor array that remains stable in solution can be realized by adhering anti-VEGF aptamers to the surfaces of micro conductive polymer nanomaterials, to which functional groups are bound, through covalent bonding. The micro conductive polymer nanomaterials conventionally developed by the present inventors (Korean Patent Application No. 10-2007-0120359) have a diameter of about 200 nm, and field-effect transistor biosensors for diagnosing cancers provided with anti-VEGF aptamers developed by the present inventors exhibited about 10-fold improved sensitivity performance, as compared to conventional biosensors for detecting VEGF based on inorganic semiconductors (zinc nanowires). However, it was found that reuse of biosensors three or more times disadvantageously causes deterioration in sensitivity. The present inventors found that nanomaterials (100 nm) that are half the size (diameter) of conventional micro conductive polymers can be prepared by controlling the temperature and reaction time, and field-effect transistor biosensors for diagnosing cancers prepared using the same are selective to VEGF, exhibit 100-fold improved sensitivity, as compared to biosensors for detecting VEGF using conventional inorganic semiconductors, and maintained sensitivity, although reused ten or more times. The present invention has completed based on the discovery.

The present invention entails forming a field-effect transistor channel region using micro conductive polymer nanomaterials functionalized with anti-VEGF aptamer and detecting VEGF in real time using the channel region.

In accordance with the present invention, provided is a method for fabricating a high-sensitivity field-effect transistor biosensor for diagnosing cancers, comprising:

(a) adding a surfactant to a nonpolar solvent at $-20°$ C. to $0°$ C.;

(b) adding an aqueous cationic oxidizing agent solution to the surfactant solution with stirring to form an oxidizing agent-adsorbed micelle having a cylindrical shape through interaction between an anionic surfactant and a cationic oxidizing agent;

(c) adding functional monomers to conductive polymer monomers dropwise to prepare micro conductive polymer nanomaterials having a cylindrical micelle surface with functional groups;

(d) fixing the nanomaterials on an electrode substrate with a surface modified through chemical reaction;

(e) adhering an anti-VEGF aptamer to the surface of nanomaterials through chemical reaction to obtain a sensor medium; and (f) providing a detector to detect variations in electrical properties of the sensor medium using field-effect transistor array through a liquid-ion gate.

In step (a), the surfactant is dissolved in the nonpolar solvent at a temperature of $-20°$ C. to $0°$ C. to form spherical micelles. The decrease in the diameter of micelles formed by reducing the activity of the surfactant at a low temperature enables diameter control of micro nanomaterials.

Preferably, the surfactant may be added in an amount of 10 to 30% by weight based on the total weight of the nonpolar solvent.

Surfactants that can be used in the present invention are not particularly limited and may be selected from most anionic surfactants applicable to emulsion polymerization. Preferred examples of surfactants include dioctyl sulfosuccinate (sodium salt, AOT), sodium dodecylsulfate (SDS), sodium dodecylbenzenesulfonate (SDBS) and the like.

The kinds of the nonpolar solvent are also not limited particularly, and preferred examples thereof include hexane, heptane, octane, benzene, toluene, xylene and the like.

In step (b), the spherical micelles are modified into cylindrical micelles through interaction with the metal salt or the oxidizing agent. An aqueous solution of the metal salt and the oxidizing agent may be suitably selected depending on the type of the surfactant used, and in particular, a substance serving as a metal salt and an oxidizing agent such as ferric trichloride ($FeCl_3$), ferric trichloride hexahydrate ($FeCl_3(H_2O)_6$), or ferric sulfate ($Fe_2(SO_4)_3$) is used in the form of a solution dissolved in water.

The aqueous solution of the metal salt and the oxidizing agent may be added in an amount of 1 to 5% by weight, based on the total weight of the surfactant and the nonpolar solvent used in step (a). In addition, the stirring is preferably carried out at $-5°$ C. to $0°$ C. for 12 hours.

In step (c), chemical copolymerization between the conductive polymer monomers and the functional monomers occurring on the surfaces of cylindrical micelles provides formation of micro conductive polymer nanomaterials. The type and incorporation level of surface functional groups can be controlled by controlling the kind and addition amount of functional monomers.

Regarding step (d), in conventional methods, polymer nanomaterials are fixed on the microelectrode array substrate through physical bonding. However, physical bonds disadvantageously cannot provide a desired level of fixing property upon practical application. Accordingly, in step (d), chemical reaction, that is, chemical bonds exhibit greater fixing effects than conventional physical bonds.

A carboxylic group (—COOH), the functional group in an amount controlled without undergoing complicated surface-modification processes can be readily incorporated into the surface of the micro conductive polymer nanomaterials prepared by the method according to the present invention. Micro conductive polymer nanomaterials are fixed by cross-linking bonds via amide bonds on the electrode substrate which is surface-modified into amine (—$NH_2$) through silane treatment using the surface functional groups. The sensor device connected by these chemical bonds induces an increased interaction between the device and target materials due to inherent large surface-area and isotropic electrical properties of micro conductive polymer nanoparticles, and considerably rapid and reproducible reactions can be observed using the sensor device.

In step (e), an anti-VEGF aptamer can also be stably fixed to the surface of nanomaterials by inducing covalent bonds via amide bonds in the same manner as in step (d). The covalent bond advantageously induces high interaction between the transducer and the target material, as compared to physical absorption. In addition, an amount of anti-VEGF aptamer incorporated can be controlled by the amount of the surface functional groups of one-dimensional conductive polymer nanomaterials.

The field-effect transistor used in step (f) is already a well-known device, which is used for detecting electrical properties between the transducer and the target material in the present study. This detects variations in current characteristics between a source and a drain depending on variations in liquid-ion gate potential, when a predetermined voltage is applied between the source and the drain. Based on this mechanism, the device conductive polymer nanomaterials functionalized with an anti-VEGF aptamer are arranged as transducers between the source and the drain, and variations in source-drain electrical properties are detected through interaction between the transducer and a target material, when the target material is incorporated and serves as a gate potential. More specifically, the target material used in this research induces electric charges through interaction with the anti-VEGF aptamer, and these charges reduce formation of holes on the surfaces of conductive polymer nanomaterials, thus reducing flow of electric current between the source and drain.

In a preferred embodiment, provided is a method for fabricating high-sensitivity field-effect transistor biosensors for diagnosing cancers wherein the conductive polymer monomers used for step (c) are selected from the group consisting of pyrrole, aniline, thiophene, and derivatives thereof and combinations thereof.

Any functional monomers may be used in step (c) without particular limitation, so long as they have functional groups which may be linked to VEGF through chemical bonds. Examples of these functional monomers include pyrrole-2-carboxylic acid, pyrrole-3-carboxylic acid, pyrrole-2-sulfonic acid, 2-aminobenzoic acid, 3-aminobenzoic acid, aniline-2-sulfonic acid, thiophene-2-carboxylic acid, thiophene-3-carboxylic acid and the like.

In step (c), the conductive polymer nanomaterials have a diameter of 50 nm to 100 nm. When the conductive polymer nanomaterials have a diameter less than 50 nm, preparation process thereof is considerably troublesome, and when the diameter exceeds 100 nm, achieving desired levels of sensitivity and reusability is difficult.

In a preferred embodiment, provided is a method for fabricating a high-sensitivity field-effect transistor biosensor for diagnosing cancers by fixing the one-dimensional nanomaterials having the predetermine functional groups in step (d) on the surface-modified electrode substrate through covalent bonding.

The channel region is where free electric charges are moved by the voltage (VDS) applied between the source and the drain and is made of a micro polymer nanomaterial.

The electrode substrate made of silicon or glass is treated with a silane coupling agent to incorporate functional groups, which may be reacted with the functional groups of the conductive polymer nanomaterials, into the surface of the electrode substrate. The kind of silane coupling agents is not limited and silane coupling agents having terminal groups suitable for covalent bonding depending on the functional groups of conductive polymer nanomaterials are thus suitably selected. Non-limiting examples of useful silane coupling agents include 3-aminopropyltrimethoxysilane, 3-aminopropyltriethoxysilane, vinyltrimethoxysilane and carboxyethylsilanetriol.

The concentration of the silane coupling agent may range from 0.01% to 10% by weight, with respect to the total weight of the solution, is not limited thereto and may be less than 0.01% by weight or higher than 10% by weight.

In another preferred embodiment, provided is a method for fabricating high-sensitivity field-effect transistor biosensors for diagnosing cancers wherein two interdigitated microelectrode bands to form a field-effect transistor array in step (f) are used as source and drain electrodes.

In step (f), the two interdigitated microelectrode bands are used as a source electrode and a drain electrode, and the channel region is made of micro conductive polymer nanomaterials. A liquid-ion gate is used and a gate electrical potential is controlled using a reference electrode and a counter electrode. Such a field-effect transistor array may vary current flow between the source and the drain through accumulation and reduction of electric charge carriers in micro conductive nanoparticles through specific reaction of anti-VEGF aptamer for diagnosing cancers with the target material, that is, vascular endothelial growth factor (VEGF). Conductive variations generated in this transducer can be quantified in real time using an electrical variation device.

In another preferred embodiment, provided is a method for fabricating a high-sensitivity field-effect transistor biosensor for diagnosing cancers wherein VEGF in step (e) is covalently bound to functional groups provided on the surface of one-dimensional conductive polymer nanomaterials.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF PREFERRED EMBODIMENTS

Hereinafter, the present invention will be described with reference to the annexed drawings and is not to be construed as being limited to the content of the drawings.

Figure 1:
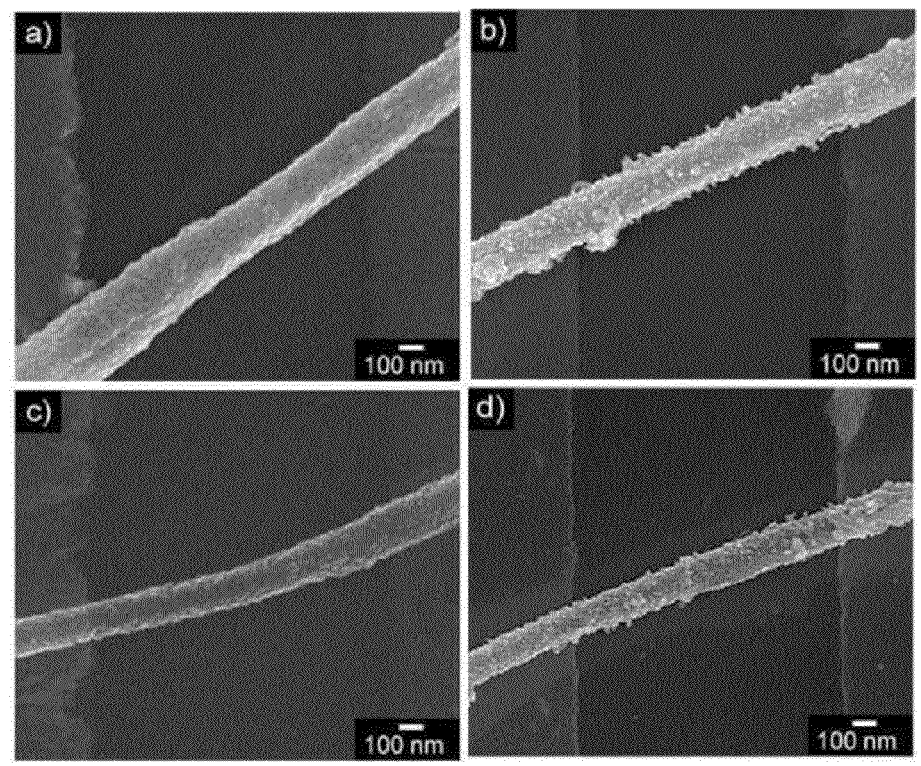
FIG. 1(a) is a scanning electron microscope (SEM) image illustrating a carboxylated polypyrrole nanotube with a size of 200 nm prepared in Comparative Example 1.
FIG. 1(b) is an SEM image illustrating a carboxylated polypyrrole nanotube with a size of 200 nm prepared in Comparative Example 1 whose surface is bound to anti-VEGF aptamer.
FIG. 1(c) is an SEM image illustrating a carboxylated polypyrrole nanotube with a size of 100 nm prepared in Example 1.
FIG. 1(d) is an SEM image illustrating a carboxylated polypyrrole nanotube with a size of 100 nm prepared in Example 1 whose surface is bound to anti-VEGF aptamer.

FIG. 1(a) is a scanning electron microscope (SEM) image illustrating a carboxylated polypyrrole nanotube with a size of 200 nm prepared in Comparative Example 1, and FIG. 1(b) is an SEM image illustrating a carboxylated polypyrrole nanotube with a size of 200 nm prepared in Comparative Example 1 whose surface is bound to anti-VEGF aptamer.

FIG. 1(c) is a scanning electron microscope (SEM) image illustrating a carboxylated polypyrrole nanotube with a size of 100 nm prepared in Example 1, and FIG. 1(d) is an SEM image illustrating a carboxylated polypyrrole nanotube with a size of 100 nm prepared in Example 1 whose surface is bound to anti-VEGF aptamer.

Figure 2:
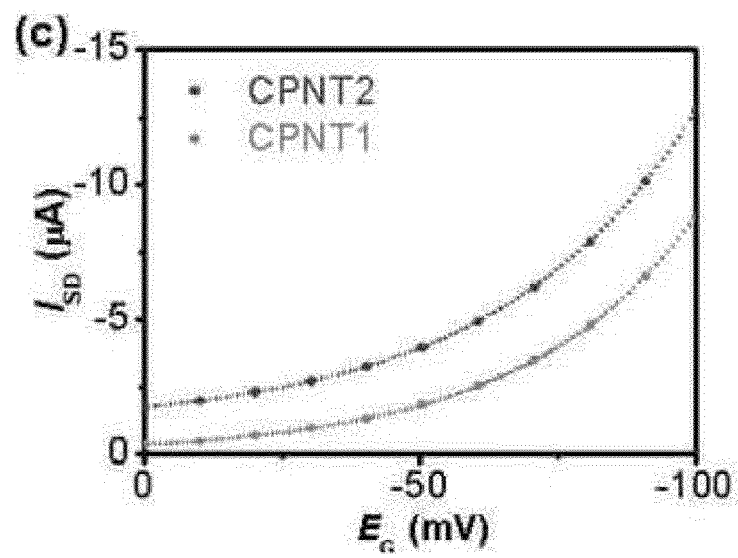
FIG. 2 shows real-time comparison results of current variations between sensors fabricated in Example 1 and Comparative Example 1 in Experimental Example 1.

FIG. 2 shows results of real-time comparison of current variations between sensors fabricated in Example 1 and Comparative Example 1 in Experimental Example 1. CPNT-1 and CPNT-2 are carboxylated polypyrrole nanotubes prepared in Comparative Example 1 and Example 1, respectively. The source, drain, liquid-ion gate and gate electric potential are represented by S, D, G and Eg, respectively.

Figure 3:
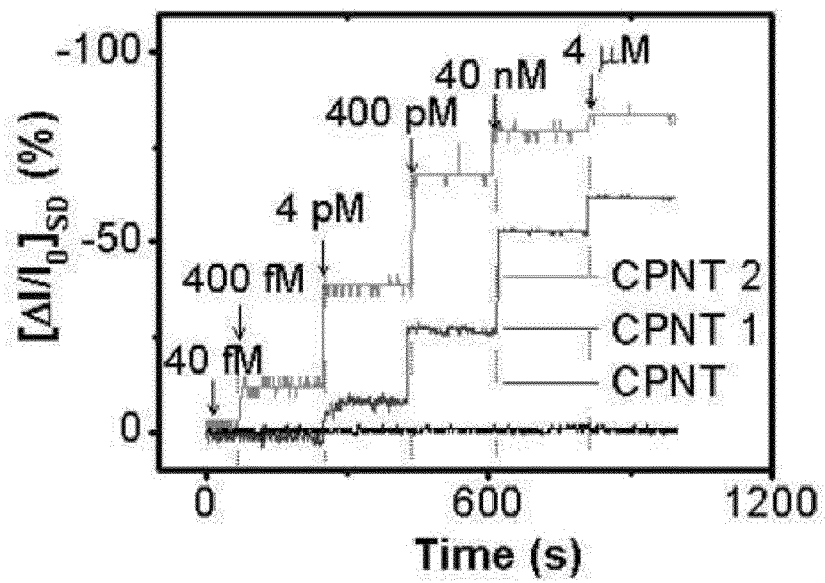
FIG. 3 is a graph showing current variation test results of sensors fabricated in Example 1 and Comparative Example 1 for VEGF in the concentration range from 4 µM to 40 fM in Experimental Example 2.

FIG. 3 is a graph showing current variation test results of sensors fabricated in Example 1 and Comparative Example 1 for VEGF in the concentration range from 4 µM to 40 fM in Experimental Example 2. CPNT-1 and CPNT-2 indicate nanomaterials wherein an anti-VEGF aptamer is linked to carboxylated polypyrrole nanotubes prepared in Comparative Example 1 and Example 1, respectively, and CPNT means polypyrrole nanotube to which anti-VEGF aptamer is not linked.

FIG. 3 shows one embodiment using VEGF. More specifically, in this embodiment, when VEGF is added dropwise to a sensor channel region containing a buffer solution, it is bound to the anti-VEGF aptamer fixed on the sensor surface and holes are depleted on the channel surface composed of micro conductive polymer nanomaterials through field effects of the electric charges of VEGF, thus causing variations in electrical conductivity and the VEGF is detected based on the variations. VEGF is negatively charged at pHs higher than the isoelectric point (PI) thereof, whereas it is positively charged at pHs lower than PI. When a pH 7.5 buffer is charged in the P-type micro conductive polymer sensor channel region and VEGF is added dropwise thereto, (+) charged VEGF depletes hole carriers of micro conductive polymer nanomaterial channels, thus causing a decrease in electrical conductivity.

Figure 4:
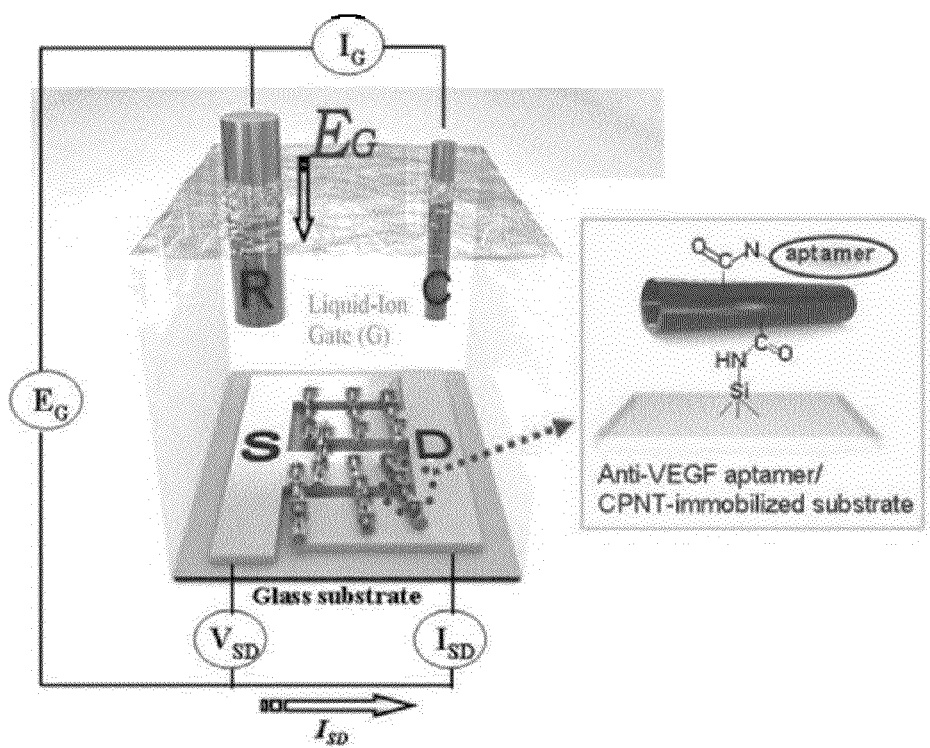
FIG. 4 is a schematic view illustrating a liquid-ion gate field-effect transistor biosensor wherein the anti-VEGF aptamer-linked micro conductive polymer nanomaterial is applied to a channel region.

FIG. 4 is a schematic view illustrating a liquid-ion gate field-effect transistor biosensor wherein the anti-VEGF aptamer-linked micro conductive polymer nanomaterial is applied to the channel region. In FIG. 4, S and D indicate a source and a drain, respectively, and R and C indicate a reference electrode and a counter electrode, respectively.

Generally, a field-effect transistor biosensor has a structure in which an insulating film is arranged on a substrate and a sensor structure to sense a target material is arranged thereon. The field-effect transistor biosensor according to the present invention, as shown in FIG. 4, includes two interdigitated microelectrode bands formed by lithography with gold, arranged on a surface-modified glass substrate, and a transducer formed using a conductive polymer nanomaterial with surface functional groups. The transducer is fixed to the glass substrate having one surface-modified surface through covalent bonds and the remaining surfaces thereof are chemically bound to anti-VEGF aptamer having high affinity to VEGF.

In accordance with the method for sensing the field-effect transistor biosensor, a predetermined voltage is applied between a source and a drain, variation in electrical conductivity caused by bonds of a target material to a sensing material is measured as current and the target material is thus detected in real time using electrical signals. The voltage applied between the source and the drain may be either DC or AC. Preferred is use of low AC voltage to avoid damage of the target and sensing materials. Depending on resistance of the sensor, the AC voltage may be preferably within the range from several tens of mV to several hundreds of mV. A fluid channel enabling the target material to be injected perpendicular to the direction of micro conductive polymer nanomaterials wherein current ($I_{SD}$) flows between the source and the drain direction is present. The fluid channel through which the sensory material is injected and interacts with the fixed micro conductive polymer nanomaterials may be composed of poly-dimethyl siloxane (PDMS), acryl, COC or the like and is filled with a biocompatible buffer solution.

The operating mechanism of the FET sensor is as follows. First, when a target material, VEGF, is added dropwise to a channel containing a buffer solution arranged on the sensor structure, the target material is selectively bound to a sensory material (anti-VEGF aptamer) fixed on a micro conductive polymer structure. At this time, the target material is electrically-charged under specific conditions and holes are accumulated or reduced in the micro conductive polymer structure through the field effect of the electric charges. This variation causes variations in electrical conductivity between the source and the drain and variations in electrical conductivity are measured using a current detector, to detect the target material.

EXAMPLES

Now, the present invention will be described in more detail with reference to the following examples. These examples are provided only for illustrating the present invention and should not be construed as limiting the scope and spirit of the present invention.

Example 1

A reactor containing 20 mL of hexane was placed in a reactor vessel adjusted to −7° C. with a thermistor, 7.9 mmol of AOT was added thereto and the resulting mixture was stirred to form micelles. An aqueous ferric trichloride solution (7M, 0.5 mL) was incorporated into the reaction mixture and a mixture of pyrrole (6 mmol) and pyrrole-3-carboxylic acid (0.4 mmol) was then slowly added dropwise thereto. The resulting mixture was stirred at −4° C. for 48 hours to perform polymerization and an excess of ethanol was added to the reactor. The reaction solution was transferred to a separatory funnel and the precipitated carboxylated polypyrrole nanoparticle layer was then collected. The carboxylated polypyrrole nanoparticles thus prepared were observed with an electron microscope. As a result, nanotube particles having a diameter of about 100 nm and a length of 5 µm or higher were observed (FIG. (c)).

An interdigitated microelectrode array was patterned on a glass substrate by photolithography. The electrode structure includes 80 finger pairs of arrays having a width of 10 µm, a length of 4,000 µm, a thickness of 40 nm and an interspacing of 10 µm. The electrode substrate was surface-modified using 5 wt % aqueous 3-aminopropyltrimethoxysilane solution for reaction with the functional groups of the micro conductive polymer nanomaterials. 10 µL of an ethanol solution containing 0.1 wt % carboxylated polypyrrole nanotubes thus obtained was mixed with 10 wt % 4-(4,6-dimethoxy-1,3,5-triazin-2-yl)-4-methylmorpholinium (DMT-MM) and the resulting mixture was exposed to the surface-modified electrode substrate. After completion of the reaction, the residue was removed with distilled water and moisture was removed using nitrogen gas.

In order to adhere an anti-VEGF aptamer to the surface-modified electrode substrate, a mixture of an aqueous DMT-MM solution (10 wt %, 10 µL) and an anti-VEGF aptamer (1 µM, 2 µL) was reacted with carboxylated polypyrrole nanotubes obtained in Examples 1 and 2. An anti-VEGF aptamer 3'-terminal is bound to an amine linker in order to form covalent bonds with carboxylic groups present on the nanotube surfaces through contraction reaction. After completion of the reaction, the residue was removed with distilled water and moisture was removed using nitrogen gas (FIG. 1 (d)).

As shown in FIG. 4, a field-effect transistor array using a liquid-ion gate (G) was realized.

Comparative Example 1

A reactor containing 20 mL of hexane was placed in a reactor vessel adjusted to 15° C. with a thermistor, 7.9 mmol of AOT was added thereto and the resulting mixture was stirred to form micelles. An aqueous ferric trichloride solution (7M, 0.5 mL) was incorporated into the reaction mixture and a mixture of pyrrole (6 mmol) and pyrrole-3-carboxylic acid (0.4 mmol) was then slowly added dropwise thereto. The resulting mixture was stirred at 15° C. for 2 hours to perform polymerization and an excess of ethanol was added to the reactor. The reaction solution was transferred to a separatory funnel and the precipitated carboxylated polypyrrole nanoparticle layer was then collected. The carboxylated polypyrrole nanoparticles thus prepared were observed with an electron microscope. As a result, nanotube particles having a diameter of about 100 nm and a length of 5 µm or higher were observed (FIG. (a)).

An interdigitated microelectrode array was patterned on a glass substrate by photolithography. The electrode structure includes 80 finger pairs of arrays having a width of 10 µm, a length of 4,000 a thickness of 40 nm and an interspacing of 10 µm. The electrode substrate was surface-modified using 5 wt % aqueous 3-aminopropyltrimethoxysilane solution for reaction with the functional groups of the micro conductive polymer nanomaterials. 10 µL of an ethanol solution containing 0.1 wt % carboxylated polypyrrole nanotubes thus obtained was mixed with 10 wt % 4-(4,6-dimethoxy-1,3,5-triazin-2-yl)-4-methylmorpholinium (DMT-MM) and the resulting mixture was exposed to the surface-modified electrode substrate. After completion of the reaction, the residue was removed with distilled water and moisture was removed using nitrogen gas.

In order to adhere an anti-VEGF aptamer to the surface-modified electrode substrate, a mixture of an aqueous DMT-MM solution (10 wt %, 10 µL) and an anti-VEGF aptamer (1 µM, 2 µL) was reacted with carboxylated polypyrrole nanotubes obtained in Examples 1 and 2. An anti-VEGF aptamer 3'-terminal was bound to an amine linker in order to form covalent bonds with carboxylic groups present on the nanotube surfaces through contraction reaction. After completion of the reaction, the residue was removed with distilled water and moisture was removed using nitrogen gas (FIG. 1 (b)).

As shown in FIG. 4, a field-effect transistor array using a liquid-ion gate (G) was realized.

Experimental Example 1

Regarding biosensors fabricated in Example 1 and Comparative Example 1, a channel region provided between a source (S) electrode and a drain (D) electrode was formed using carboxylated polypyrrole nanotubes. A source-drain voltage was applied using a potentiostat connected to a computer, and current variation ($\Delta I/I0=(I-I0)/I0$, I and I0 indicate a current and an initial current value measured in real-time, respectively) was monitored in real time.

As a result, it was confirmed that the micro carboxylated polypyrrole nanotube (CPNT2) channel region fabricated at a lower temperature (Example 1), as compared to conventional cases exhibited higher conductivity than that of the nanomaterial (CPNT1) prepared in Comparative Example 1 (FIG. 2).

Experimental Example 2

To investigate the action of anti-VEGF aptamer for diagnosing cancers on biosensors fabricated in Example 1 and Comparative Example 1, polypyrrole nanotubes, to which anti-VEGF aptamer for diagnosing cancers was not adhered, were applied to the channel region. As a result, as shown in FIG. 3, when VEGF (Vascular Endothelial Growth Factor) was injected, no variation in source-drain current was observed. This means that selective reaction between anti-VEGF aptamer for diagnosing cancers and VEGF causes variation in source-drain current.

Experimental Example 3

VEGF with a concentration of 4 µM to 40 fM was injected into the biosensor in Comparative Example 1. A source-drain current variation was investigated, and as shown in FIG. 3, a testing curve was recorded within the corresponding concentration range.

Experimental Example 4

A test was performed in the same manner as in Experimental Example 3 except that the biosensor of Example 1 was used. As a result, as shown in FIG. 3, a testing curve in the corresponding concentration range was recorded.

Experimental Example 5

Unlike experimental Examples 3 and 4, sensitivity tests were performed. As a result, it was conformed that Experimental Example 3 exhibited sensitivity at VEGF concentration of 4 pM, whereas Experimental Example 4 exhibited sensitivity at VEGF concentration of 40 pM. This means that the field effect transducer biosensor for diagnosing cancers using the micro polymer transistor fabricated according to the present invention exhibits 100-fold superior performance as compared to VEGF detection biosensors using conventional zinc nanowires.

INDUSTRIAL APPLICABILITY

As apparent from the above description, the present invention provides high-sensitivity field-effect transistor biosensors for diagnosing cancers which have a ½ decreased diameter, as compared to micro conductive polymer nanomaterials developed by the present inventors, and exhibit considerably superior selective-specificity to VEGF, high-sensitivity enabling detection of a considerably low concentration of VEGF and superior reusability such as performance maintenance upon repeated reuse.

In addition, a high-sensitivity field-effect transistor biosensor for diagnosing cancers can be readily fabricated by using the method according to the present invention. An assay method for diagnosing cancers using micro polymer nanomaterial transistor arrays enables detection of VEGF with a considerably small amount of blood, as compared to conventional immunotherapy.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for fabricating a high-sensitivity field-effect transistor biosensor for diagnosing cancers, comprising:
   (a) adding a surfactant to a nonpolar solvent at $-20°C$ to $0°C$;
   (b) adding an aqueous solution of a metal salt and an oxidizing agent to the surfactant solution with stirring to form micelles having a cylinder shape;
   (c) adding conductive polymer monomers and functional monomers to be copolymerized to the micelles dropwise to prepare one-dimensional conductive polymer nanomaterials with controlled surface functional groups;
   (d) fixing the nanomaterials on an electrode substrate with a surface modified through chemical reaction;
   (e) adhering an anti-VEGF aptamer to the surface of the nanomaterials through chemical reaction to obtain a sensor medium; and
   (f) providing a detector to detect variations in electrical properties of the sensor medium using a field-effect transistor array through a liquid-ion gate.

2. The method according to claim 1, wherein the conductive polymer monomers are selected from pyrrole, aniline, thiophene and derivatives thereof.

3. The method according to claim 1, wherein the functional monomers have a functional group linkable to VEGF through a chemical bond.

4. The method according to claim 1, wherein the conductive polymer nanomaterials have a size of 50 to 100 nanometers.

5. The method according to claim 1, wherein the one-dimensional nanomaterials having a functional group are fixed on the electrode substrate with a surface modified through covalent bonding, to form a channel region.

6. The method according to claim 1, wherein the field-effect transistor array is formed using two interdigitated microelectrode bands as a source electrode and a drain electrode.

7. The method according to claim 1, wherein VEGF is covalently bound to the surface functional groups of the one-dimensional conductive polymer nanomaterials.

* * * * *